United States Patent [19]

McDaniel et al.

[11] Patent Number: 5,220,104
[45] Date of Patent: Jun. 15, 1993

[54] METHOD FOR THE PREVENTION OF FOULING IN A CAUSTIC SOLUTION

[75] Inventors: Cato R. McDaniel, The Woodlands; Paul V. Roling, Spring, both of Tex.

[73] Assignee: Betz Laboratories, Inc., Trevose, Pa.

[21] Appl. No.: 898,976

[22] Filed: Jun. 15, 1992

[51] Int. Cl.$^5$ ............................................. C07C 7/00
[52] U.S. Cl. ................................. 585/853; 585/833; 585/864; 585/868; 423/245.1
[58] Field of Search ............... 585/853, 833, 864, 868; 423/245.1

[56] References Cited

U.S. PATENT DOCUMENTS

| | | | |
|---|---|---|---|
| 3,281,489 | 10/1966 | Goering | 260/681.5 |
| 3,308,201 | 3/1967 | Bowers et al. | 260/681.5 |
| 3,336,414 | 8/1967 | Woerner | 260/681.5 |
| 3,535,399 | 10/1970 | Tabler | 260/681.5 |
| 3,793,187 | 2/1974 | Marx et al. | 208/289 |
| 3,801,669 | 4/1974 | Christmann | 260/680 |
| 3,998,902 | 12/1976 | Foster et al. | 585/853 |
| 4,125,568 | 11/1978 | Theriot et al. | 585/853 |
| 4,673,489 | 6/1987 | Roling | 208/289 |

*Primary Examiner*—Anthony McFarlane
*Assistant Examiner*—Nhat D. Phan
*Attorney, Agent, or Firm*—Alexander D. Ricci; Richard A. Paikoff

[57] ABSTRACT

The present invention is directed to the use of a solution of a percarbonate compound to prevent fouling during the basic washing of hydrocarbons containing oxygenated compounds. More specifically, oxygenated compounds such as carbonyl containing organics have a tendency to polymerize, producing fouling elements when such are contained in hydrocarbons being washed with basic materials. Solutions of percarbonate compounds are quite effective in reducing the fouling tendencies due to these specific mechanisms.

11 Claims, No Drawings

METHOD FOR THE PREVENTION OF FOULING IN A CAUSTIC SOLUTION

This invention relates to the prevention of fouling in a caustic solution which is in contact with a gaseous or liquid hydrocarbon stream.

BACKGROUND OF THE INVENTION

In cracking operations, (pyrolysis) such as in the cracking of ethane, propane and naphthas to olefins, oxygenated compounds, including carbonyl compounds, are formed. The amount of carbonyl compounds, such as aldehydes and ketones, formed in such an operation can vary widely, but is typically 1-100 ppm in the gas stream with concentrations as high as 1000 ppm occasionally being encountered. The carbonyl level is dependent on the type of feedstock used and cracking temperatures. When the gas stream is passed through a basic wash (pH > 7) to remove acidic components such as hydrogen sulfide and carbon dioxide, oxygenated compounds and carbonyl compounds are also removed. These oxygen compounds, particularly acetaldehyde, will undergo polymerization in the presence of the base.

In the wash tower, the polymer will settle on the trays resulting in a loss of heat transfer efficiency, necessitating a costly shutting down of the unit in order to clean the trays. The type of basic wash systems where treatment is required to inhibit fouling include amine acid gas scrubber (e.g., MEA, DEA, isopropyl amine, butyl amine, etc.) and caustic wash systems.

PRIOR ART

U.S. Pat. Nos. 3,336,414 and 3,308,201 disclose processes utilizing aqueous caustic washes (pH > 10) of carbonyl - contaminated hydrocarbons in order to remove carbonyl compounds.

In U.S. Pat. No. 3,281,489, carbonyl compounds are removed from a butadiene stream (obtained from the pyrolysis of saturated hydrocarbons) by selective hydrogenation to reduce some of the carbonyls. This is followed by caustic washing to remove substantially all of the remaining carbonyl compounds. If the caustic washing is performed before the hydrogenation, carbonyl polymeric materials from aldol condensation foul the process equipment. U.S. Pat. No. 3,801,669 discloses the use of cement to extract carbonyl compounds from hydrocarbon streams.

The extraction of carbonyl compounds at acid pH from hydrocarbon streams by aqueous solutions of hydrazine compounds is reported in U.S. Pat. No. 3,793,187. The carbonyl compounds need to be extracted because they have an inhibiting effect on further processing steps. Extractions of only liquid systems are contemplated in this reference.

In U.S. Pat. No. 3,535,399, carbonyl compounds are removed from gaseous hydrocarbon streams by contacting the streams with an aqueous solution of sodium hydroxide and urea. The caustic removes acid materials and the urea complexes with the carbonyl compounds to form aldehyde-urea and ketone-urea resins that are entrained in the aqueous solution.

SUMMARY OF THE INVENTION

In accordance with the invention, a solution of a percarbonate of a Group I or Group II metal is used to inhibit the formation and deposition of fouling materials during the basic washing of hydrocarbons contaminated with oxygenated compounds. All components are commercially available.

DETAILED DESCRIPTION OF THE PREFERRED EMBODIMENTS

After reviewing the problems associated with carbonyl contamination of hydrocarbons, particularly the gaseous olefins derived from pyrolytic cracking, it was apparent to the present inventors that the cracking industry required a treatment which would control the formation and deposition of fouling materials during the basic wash of hydrocarbons. Most desirably, the treatment would be such that it would operate effectively in the highly basic wash to alleviate the potential problems due to the oxygenated compounds, particularly the carbonyls without the formation of other solid materials which had to be removed. The treatment not only had to be effective but also cost-effective.

The present inventors have discovered a method of inhibiting the formation and deposition of fouling materials during the basic wash and in particular the caustic wash of hydrocarbons containing oxygenated compounds, and in particular the gaseous olefins containing carbonyl compounds. The latter carbonyl compounds under basic conditions undergo, in many instances, Aldol condensation reactions to produce polymeric materials which deposit on the equipment and in particular plug the trays in the caustic wash tower.

The present invention is particularly appropriate for the basic washing process which follows the pyrolytic cracking of such hydrocarbons as ethane, propane, butane, naphtha and mixtures thereof to produce the corresponding gaseous ethylene, propylene, butadiene, etc., containing the carbonyl as well as other contaminants.

The basic washing generally entails contacting in wash towers an aqueous basic solution with the gaseous olefins to remove any hydrogen sulfide, carbon dioxide, and other oxygenated compounds. As previously discussed, the conditions are such as to be conducive for condensation reactions of any aldehydes/ketones (acetaldehyde) contained therein.

Oxidizing agents that can be used in the invention are any compounds that will be specific for carbonyls, will not contribute solids, and will not interact with the olefins. (Therefore, ozone, e.g., is not useful as it will react with olefins). Materials with transition metals will generally form solid metal oxides.

Suitable oxidizing agents include percarbonates of Group I and Group II metals, such as sodium percarbonate and potassium percarbonate.

The above-identified inhibitors may be added to the caustic towers as neat materials or as solutions. The preferred method of addition is as an aqueous solution with about 2 to 35 weight percent inhibitor present, so that safety problems are minimized and an accurate metering of the inhibitor to the tower can be achieved. The fouling inhibitors can be used in a continuous or batch process. For one mole of carbonyl compound, one mole of inhibitor is needed. However, since other unknown side reactions could consume the inhibitor, a molar ratio greater than 1:1 should be used. In general, a molar ratio of from about 1:1 to 10:1 of inhibitor to carbonyl content should suffice, with a preferred ratio of from about 1:1 to 3:1.

A preferred formulation of the percarbonate compound for addition to the basic wash would on a weight basis comprise 10% sodium percarbonate and 90% water. This product would be added to the wash in quantities to assure that the molar ratio of sodium percarbonate to oxygenated or carbonyl compound is 1:1 or greater. Treatment ranges of from about 1 to 10,000 parts of product per million of wash solution could be utilized.

EXPERIMENTAL

The following examples are given to illustrate the invention, but are not meant to be limiting.

In a test tube were placed the appropriate amount of sodium percarbonate, 10 milliliters of 10% sodium hydroxide solution, and 0.50 milliliters of vinyl acetate (5.4 mmols), respectively. The solutions were observed for one day, with the data in the table below being noted.

| Grams of Percarbonate (mmols of $H_2O_2$) | Solution Changes |
|---|---|
| 0.00 (0.0) | Yellow color with precipitate |
| 0.28 (2.3) | Brown color with precipitate |
| 0.57 (4.7) | Brown color with precipitate |
| 0.84 (6.9) | Brown color but no precipitate |
| 1.14 (9.4) | No color and no precipitate |

Under the base conditions of the above test, vinyl acetate hydrolyzes to acetaldehyde, which in turn undergoes the aldol condensation reaction to produce colored (yellow, orange, brown) polymer. Based on the data in the table, fouling (precipitate) is prevented when enough peroxide (greater than 5.4 mmols) is present to oxidize the aldehyde.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

We claim:

1. A method for inhibiting the formation and deposition of fouling materials during basic washing of hydrocarbons contaminated with oxygenated compounds which comprises performing the washing of the hydrocarbons in the presence of a solution comprising a percarbonate compound in an amount sufficient to inhibit the formation and deposition of fouling materials.

2. The method as recited in claim 1 wherein the percarbonate compound is selected from the group consisting of sodium percarbonate and potassium percarbonate.

3. The method as recited in claim 1 wherein the hydrocarbons being washed are produced by the pyrolytic cracking of other hydrocarbons.

4. The method as recited in claim 3 wherein said other hydrocarbons are selected from the group consisting of ethane, propane, butane, naphtha or mixtures thereof.

5. The method as recited in claim 4 wherein the hydrocarbons being washed contain olefins contaminated with oxygenated compound impurities.

6. The method as recited in claim 5 wherein the hydrocarbons being washed are in a gaseous state.

7. The method as recited in claim 6 wherein the oxygenated compounds are comprised primarily of carbonyl compounds which polymerize to produce the fouling materials under basic washing conditions.

8. The method as recited in claim 7 wherein the carbonyl compounds are aldehydes, ketones or mixtures thereof.

9. The method as recited in claim 7 wherein the solution of percarbonate compound is added to the basic washing in an amount representing a molar ratio of (a) said solution of percarbonate compound to (b) said carbonyl compound of from about 1:1 to 10:1.

10. The method as recited in claim 9 wherein the molar ratio of (a) to (b) is from about 1:1 to 3:1.

11. The method as recited in claim 9 wherein the molar ratio of (a) to (b) is about 1:1.

* * * * *